United States Patent [19]

Scheffler et al.

[11] Patent Number: 5,232,919

[45] Date of Patent: Aug. 3, 1993

[54] AZELASTINE EMBONATE AND COMPOSITIONS WHICH CONTAIN IT

[75] Inventors: Gerhard Scheffler, Hanau; Dieter Sauerbier, Werther; Jürgen Engel, Alzenau, all of Fed. Rep. of Germany

[73] Assignee: Asta Pharma Aktiengesellschaft, Fed. Rep. of Germany

[21] Appl. No.: 598,742

[22] Filed: Oct. 15, 1990

Related U.S. Application Data

[63] Continuation of Ser. No. 267,568, Nov. 7, 1988, abandoned.

[30] Foreign Application Priority Data

Nov. 13, 1987 [DE] Fed. Rep. of Germany ....... 3738641

[51] Int. Cl.5 ..................... A61K 31/55; C07D 413/00
[52] U.S. Cl. .................................... 514/212; 514/826; 540/599
[58] Field of Search ................. 514/212, 826; 540/599

[56] References Cited

U.S. PATENT DOCUMENTS

| | | | |
|---|---|---|---|
| 2,925,417 | 2/1960 | Elslager et al. | 424/10 |
| 3,813,384 | 5/1974 | Vogelsang et al. | 260/239 A |
| 4,704,387 | 11/1987 | Engel et al. | 540/598 |

FOREIGN PATENT DOCUMENTS

289939A 11/1988 European Pat. Off. ............ 540/599

OTHER PUBLICATIONS

J. Allergy Clin. Immunol. (Nov. 1988) p. 801, Multicenter, Double Blind, ..., Efficacy & Safety Trial of Azelastine, Chlorpheniramine & Placebo ... Weiler M. D.

M. Negwer: Org.-Chem. Drugs and Their Synonyms, vol. III, No. 6496, 1987, p. 1145.

German Search Report re: P 37 38 681.6.

*Primary Examiner*—Leonard Schenkman
*Attorney, Agent, or Firm*—Cushman, Darby & Cushman

[57] ABSTRACT

An embonic acid salt of azelastine is disclosed which does not possess the bitter taste of azelastine, and which therefore is suitable for orally administered formulations.

12 Claims, 2 Drawing Sheets

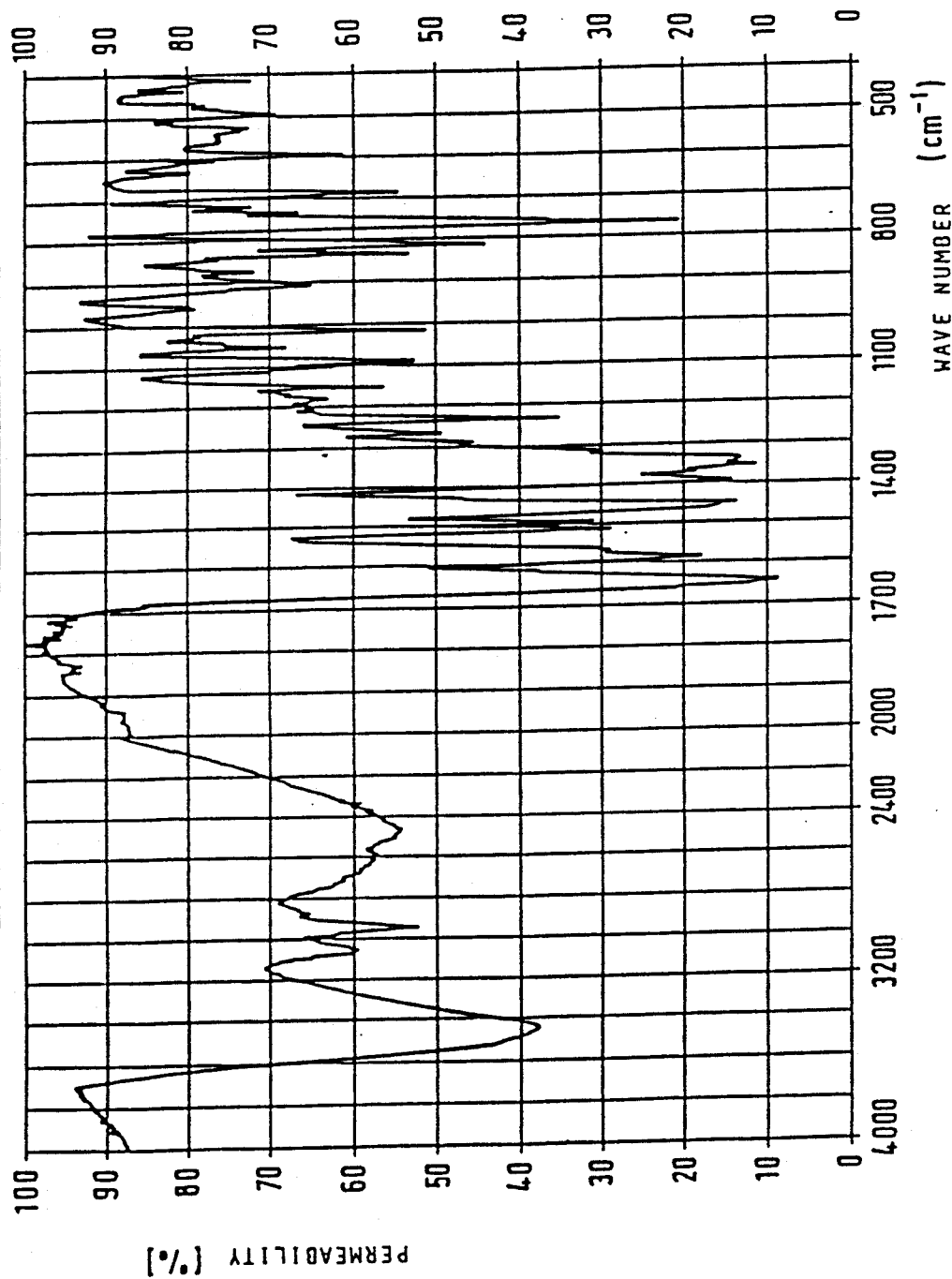

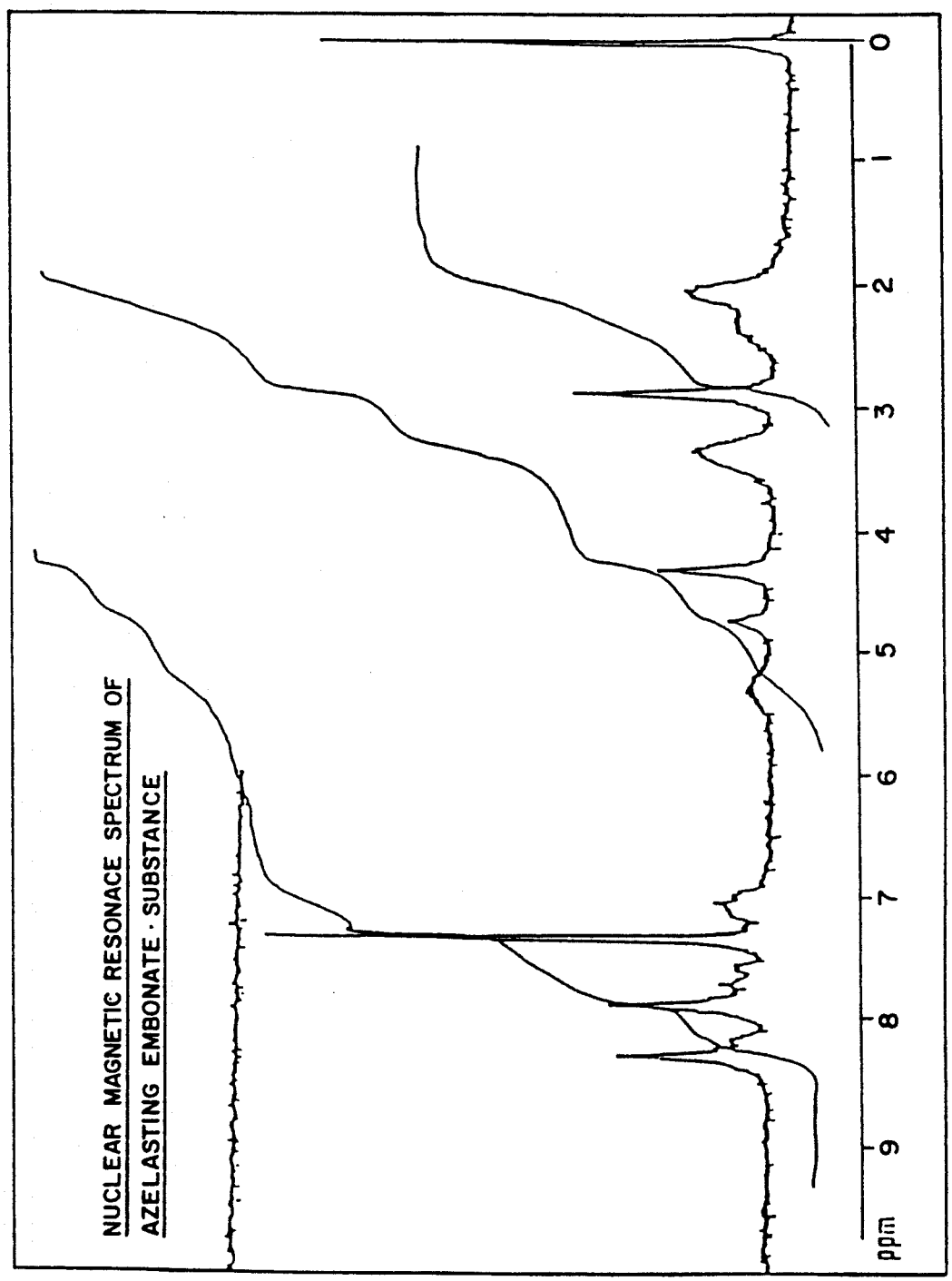
FIG. 2 NUCLEAR MAGNETIC RESONACE SPECTRUM OF AZELASTING EMBONATE · SUBSTANCE

AZELASTINE EMBONATE AND COMPOSITIONS WHICH CONTAIN IT

This is a continuation of U.S. application Ser. No. 07/267,568, filed on Nov. 7, 1988, abandoned.

The present invention relates to a derivative of azelastine which does not possess the penetrating bitter taste of azelastine, and which therefore is suitable for orally administered pharmaceutical compositions.

BACKGROUND OF THE INVENTION

Azelastine is an active substance having an anti-allergic and asthma-prophylactic effect. The chemical designation is:

4-(p-chlorobenzyl)-2-hexahydro-1-methyl-azepine-4-yl-1-(2H)-phthalazinone (See German Patent No. 21 64 058).

An important mode of administration of azelastine as an anti-allergic agent is orally, in particular in the form of tablets, capsules.

On the other hand, it has not been practical to use azelastine in the form of solutions or suspensions, because azelastine has such a penetrating, bitter taste that patients would refuse to take such azelastine solutions or azelastine suspensions orally. It has also proved impossible to overcome this bitter taste through conversion into a wide variety of salts.

SUMMARY OF THE INVENTION

In accordance with the present invention, it has now been found that azelastine, on conversion into the salt with embonic acid, can be converted into a product which no longer possesses the penetrating bitter taste of azelastine. The product, therefore, is suitable for use in, for example, orally administered formulations. Azelastine embonate is a salt of azelastine with embonic acid which is composed of 2 moles of azelastine and 1 mole of embonic acid (see Example 1).

The azelastine embonate of the invention is particularly suitable for the preparation of orally administered pharmaceutical formulations of azelastine in the form of stable suspensions, for example in the form of a juice. The embonate of the invention can naturally also be used for the preparation of other pharmaceutical formulations of azelastine such as, for example, tablets, capsules or sprays.

Should the azelastine embonate of the invention be used for the preparation of aqueous suspensions, these are suspensions which contain as active substance 3 to 3,000 mg, preferably 15 to 240 mg, in particular 60 to 120 mg (i.e. parts by weight) of azelastine embonate for each 100 ml (parts by volume) of suspension. For this purpose, the azelastine embonate preferably has a particle size under 100 μm. The pH value of such a suspension lies in the range of 3 to 9, preferably 5 to 8, in particular 6 to 7.

An particularly favorable form of azelastine embonate suspension is a thixotropic system which has high viscosity while stationary. The structure of the suspension collapses, however, when a stress is applied (for example on pouring), so that the suspension (for example the juice) becomes free-flowing.

Swelling agents, for example, are used in the preparation of such a thixotropic suspension in water. Such swelling agents are, for example: natural macromolecules (for example alginates, pectins, tragacanth, hydrocolloidal polysaccharides such as xanthane rubber), semi-synthetic macromolecules (such as cellulose ether), synthetic macromolecules (for example polyacrylates, polyvinylpyrrolidone) as well as inorganic hydrogen sources (for example colloidal silicic acid, bentonite). These swelling agents may be used individually or in mixtures. On the basis of their pronounced thixotropic properties, formulations with xanthane rubber have been found particularly suitable for the preparation of stable, free-flowing suspensions.

These swelling agents may be used individually or in a mixture. The total amount of swelling material in relation to 100 ml of suspension is, for example, 0.1 to 10, preferably 0.5 to 5 grams.

When xanthane rubber is used, the amount of xanthane rubber is, for example, 0.1 to 3, preferably 0.3 to 1.5, in particular 0.5 to 1 g, in polyacrylates 0.1 to 1 g, in alginates and tragacanth 0.1 to 0.2 g, in pectins and cellulose ethers 0.5 to 5 g, in polyvinylpyrrolidone and inorganic hydrogen formers 1 to 10 g (in each case for each 100 ml of suspension).

Furthermore, the azelastine embonate suspensions of the present invention optionally contain preservatives, sweeteners, flavorings and coloring agents conventionally used in pharmaceutical formulations.

Preservatives that may, for example, be used are organic acids (for example sorbic acid, benzoic acid), phenols (for example lower alkyl p-hydroxybenzoates), organic mercury compounds (for example thiomer sal), quaternary ammonium compounds (for example benzethonium chloride), aromatic and aliphatic alcohols (for example 1,2-propylene glycol, benzyl alcohol), chlorohexidine. The preservatives can also be used in the form of their salts (for example alkali salts such as sodium benzoate) and, of course, also as mixtures.

The amount of preservative in 100 ml of suspension may, for example, lie in the case of sorbic acid between 0.5 g and 1.0 g, benzoic acid 0.1 g and 0.2 g, thiomer sal 0.001 g and 0.091 g, benzethonium chloride 0.005 g to 0.02 g, to 1,2-propylene glycol 10 g and 30 g, benzylalcohol 1.0 g and 2.0 g, chlorohexidine 0.001 to 0.01 g.

A mixture of p-hydroxybenzoic acid lower alkyl esters is preferably used. The sum of p-hydroxybenzoic acid lower alkyl esters for each 100 ml of suspension lies, for example, between 0.1 and 0.3 g, preferably between 0.15 g and 0.25 g, in particular between 0.15 g and 0.20 g.

Sweeteners that may, for example, be used are: saccharine, cyclamate, aspartane, fructose, saccharose, sorbitol, mannitol as well as, preferably, xylitol. The amount of sweetener naturally depends on the sweetening value. Generally the amount, related to 100 ml of suspension, is 0.005 to 0.1 for saccharin, 0.5 to 2.0 for cyclamate, 0.005 to 0.3 for aspartane, 1.0 to 60 g for fructose, saccharose, sorbitol and mannitol. In the case of xylitol, this amount is, for example, 1 to 60, preferably 15 to 60, in particular 30 to 40 g.

Flavorings that may be used are: essential oils (for example peppermint oil, balm mint oil, lemon oil), fruit extracts (for example lemon, grapefruit, pineapple), aromatic drug extracts (licorice root, aniseed, fennel), natural and synthetic flavorings. Raspberry flavoring has, for example, been found to be particularly suitable.

The amount of flavoring is, for example, for each 100 ml of suspension, from 0.001 to 5 or also 10, preferably 0.01 to 1, in particular 0.01 to 0.1 g. In the case of raspberry flavoring 0.01 to 0.1, preferably 0.01 to 0.05, in particular 0.02 to 0.04 g per 100 ml of suspension are, for example, possible.

Possible coloring agents are, for example: the conventional certified pharmaceutically-acceptable, food coloring agents, coloring agents of natural foodstuffs (for example curcumin riboflavin, chlorophyll, xanthophylls), synthetic organic coloring agents (azo dyes, azo coloring lacquers), inorganic synthetic coloring agents (for example titanium dioxide, iron oxide). Synthetic azo dyes such as, for example, amaranth have proved to be particularly suitable.

The amount of coloring agents may, for example, lie between 0.001 and 1.0, preferably 0.001 and 0.1, in particular 0.001 and 0.01 g, for each 100 ml of suspension. For amaranth 1 to 10, preferably 1 to 5, in particular 2 to 4 mg are, for example, possible in relation to 100 ml of suspension.

Adjustment of the required pH value is appropriately effected using inorganic acids (hydrochloric acid, sulphuric acid, phosphoric acid), organic acids (for example citric acid, maleic acid), inorganic bases (for example sodium hydroxide solution, potassium hydroxide solution) or by means of the salts conventionally used therefor, for example ammonium chloride, sodium citrate, sodium dihydrogenphosphate).

For the preparation of suspensions of the azelastine embonate of the invention it is possible to use water as well as other physiologically acceptable liquids. Such liquids may, for example, be: monovalent and multivalent lower alcohols, such as ethanol, propylene glycol, glycerine and polyglycols with molecular weights of 200 to 600. It is also possible to use mixtures of these liquids with each other as well as with water.

Possible liquid carrier substances may also, for example, be: natural oils (for example olive oil), synthetic and semi-synthetic oily pharmaceutical liquid carries such as triglycerides of saturated plant acids with 8 to 12 carbon atoms and their mixtures.

Preferably, these are purely aqueous suspensions.

Should mixtures of water and other liquids be used, these are, for example, mixtures wherein the content of the non-aqueous proportion is 1 to 60, preferably 10 to 40, in particular 20 to 30 percent by weight, in relation to 100 grams of suspension.

Wetting agents may optionally also be added to the suspensions of the invention. Wetting agents that may be used are, for example; anionic surfactants, for example soaps, fatty alcohol sulfates, nonionic surfactants, for example polyethylene glycol fatty acid esters (Myrj), polyethylene glycol fatty alcohol ethers (Brij), sorbitan fatty acid esters (Span), polyethylene glycol sorbitan fatty acid esters (Tween), polyethylene glycol-polypropylene glycol derivatives (Pluronics).

Sorbitan fatty acid esters (with saturated or unsaturated aliphatic carboxylic acids of $C_{10}$ to $C_{20}$, polyoxyethylene fatty alcohol ethers (alcohols of $C_{10}$ to $C_{20}$) and polyethylene glycol-sorbitan carboxylic acid esters (saturated or unsaturated aliphatic carboxylic acids of $C_{10}$ to $C_{20}$) are preferably used.

The amount of wetting agent, for each 100 ml of suspension may, for example, be: 1 to $10^{-5}$, preferably 0.5 to 0.001 in particular 0.1 to 0.01 g. The wetting agent has the function of ensuring optimum dispersion of the non-dissolved active substance. Optionally, the required amount of the appropriate wetting agent should be ascertained during preliminary trials.

The azelastine embonate suspensions of the invention have, for example, viscosities in a range of 0.05 to 0.22, preferably 0.09 to 0.18, in particular 0.12 to 0.15 Pascal seconds (Pa.s.) at a shearing speed of 110 per second in the rotation viscosimeter.

It is, moreover, possible to add additional embonic acid to the axelastine embonate suspensions of the invention. Per 100 ml of suspension it is, for example, possible to add 1 to 2,000 mg, preferably 20 to 1,000 mg, in particular 50 to 150 mg of additional embonic acid to the azelastine embonate already present. The surplus embonic acid surprisingly effects an improvement in taste.

For the preparation of suspension with propellants (aerosols) the conventional propellants (propane, butane, fluorochlorohydrocarbons) are used in addition to or in place of the auxiliary substances mentioned. For such suspensions, the azelastine embonate should, for example, have a particle size with diameters between 5-10 $\mu$m.

The preparation of such aerosols is, for example, effected by dispersing 3 to 3,000 mg of azelastine embonate in 100 ml of a mixture of chlorinated fluorinated hydrocarbons and/or hydrocarbons with addition of 0.25 to 3 g of sorbitan trioleate as well as optionally with other auxiliary substances. This dispersing may be effected at a temperature between $-55°$ C. and $+55°$ C. The suspension thus obtained is filled into containers which are or will be closed with metering valves which release 0.025 to 0.1 ml of the suspension per actuation. The preparation of azelastine embonate of the required particle size is effected through grinding in a conventional micronizing apparatus.

For the preparation of other oral formulations of azelastine embonate the conventional pharmaceutical and galenically used auxiliary or carrier agents are used. For tablets, for example, the following auxiliary and carrier agents are used (amounts in percent by weight per tablet).

Fillers (5–95%): for example starch, cellulose, lactose, saccharose, fructose, sorbitol, mannitol, calcium phosphate.

Binders (1–80%): gelatin, cellulose ether, pectins, alginates, polyvinylpyrrolidone, lactose, microcrystalline cellulose.

Disintegrants (1–10%): alginates, starch, pectins, carboxymethyl cellulose, polyvinyl polypyrrolidone, ultramylopectin, bentonite.

Lubricants (0.2–10%): stearic acid, stearate, polyglycols, talcum, highly disperse silicon dioxide.

Tablets may also contain: anti-adhesion agents, absorption accelerators, hydrophilization agents, wetting agents and equivalent agents.

Coated tablets may be manufactured which, for example, also contain conventional film formers and coating materials as well as dyestuffs, softeners, polishing agents.

The fillers, binders and lubricants mentioned may also be used in the other oral medicinal forms (capsules, granulates and the like).

Tablets as well as other oral formulations (capsules, granulates) contain, for example, between 0.5 and 30 mg, preferably 1 and 20 mg, in particular 1.5 and 12 mg of azelastine embonate.

The preparation of the embonate of the invention is effected through conversion of azelastine or an acid addition salt of azelastine with embonic acid or a salt of embonic acid in an appropriate solvent with optional heating. The conversion is effected at temperatures of 18° to 150° C., in particular 20° to 100° C., preferably between 20° to 50° C.

Solvents that may be used are, for example: lower aliphatic $C_1$-$C_6$-alcohols (methanol, ethanol, propanol, isopropanol, butanol), lower aliphatic ketones with 3 to 8 carbon atoms (acetone, methylethylketone), glycolether, cyclic ethers (dioxan, tetrahydrofuran), esters of lower aliphatic carboxylic acids with lower aliphatic alcohols, amides and N-alkyl-substituted amides of aliphatic $C_1$-$C_4$-carboxylic acids (dimethylformamide, dimethylacetamide), $C_1$-$C_6$-dialkylsulfones (dimethylsulfone, tetramethylene sulfone), $C_1$-$C_6$-dialkylsulfoxides (dimethylsulfoxide) as well as other aprotic solvents such as N-methylpyrrolidone, tetramethylurea, hexamethylphosphoric acid triamide, acetonitrile, mixtures of these agents with each other as well as mixtures of one or more of them with water. In the case of aqueous mixtures the proportion of water is generally not higher than 30 percent by volume. The conversion can moreover also occur in alcohol-ether mixtures, in which case, for example, aliphatic $C_2$-$C_6$-ethers and cyclic ethers can be used. Conversion is also possible into mixtures of lower aliphatic alcohols with halogenated aliphatic or aromatic hydrocarbons.

Azelastine and embonic acid are used in a ratio of 2:1. Preference is given to the use of an excess of azelastine of 1-20, in particular 1-5% in relation to the amount of embonic acid which is necessary for the above mentioned ratio.

Should the azelastine be used in the form of its salt, salts with the following acids are, for example, possible: strong and medium-strong inorganic acids (halohydric acids such as HCl, HBr, nitric acid, phosphoric acids, sulphuric acid), strong to weak organic acids such as aliphatic and aromatic sulphonic acids (methane sulphonic acid, toluene sulphonic acid), aliphatically saturated and unsaturated single and multibasic carboxylic acids, aromatic carboxylic acids (benzoic acid, toluenecarboxylic acid).

The embonic acid may also be used in the form of a salt. Salts of embonic acid which can, for example, be used are: alkali metal salts (Na, K, Li), alkaline earth metal salts, magnesium salts, ammonium salts, alkylammonium salts.

The preparation of the pharmaceutical azelastine embonate formulations is effected through mixture or homogenization of the azelastine embonate with the remaining auxiliary and carrier substances at temperatures between 15 and 80, preferably 18 to 40, in particular 20° to 30° C. In order to reduce the pathogens (sterilization) it is optionally possible to heat for 15 to 60 minutes to 80 to 140, preferably 110° to 125° C.

For the preparation of suspensions it is, for example, possible to proceed as follows: the swelling agent (0.1 to 10, preferably 0.3 to 1.5 g per 100 ml of suspension and optionally one part of the other auxiliary substance) are dissolved in water or in the other liquids or mixtures of liquids mentioned at 20° to 30° C. The amount of water or the amount of liquid is so measured that the finished suspension contains 0.03 to 30, preferably 0.4 to 6, in particular 0.8 to 1.2 liters of water or liquid for each 1 g of azelastine embonate. The aqueous solution so obtained may then be heated for 10 to 120, preferably 15 to 60 minutes to 80° to 134° C., preferably 20 to 30 minutes to 110° to 121° C.

Following cooling to 25° to 35° C., a wetting agent is optionally added to this solution followed by the mixture of the azelastine embonate and optionally the preservatives, sweeteners, dyestuffs and optionally flavorings and other auxiliary and/or carrier substances prepared at temperatures of 20° to 30° C. and the result homogenized (temperature 15° to 35° C., preferably 20° to 30° C.).

This process is optionally followed by the addition of flavorings as well as adjustment of the pH value to 3 to 9.

The preparation of the above-mentioned azelastine embonate suspension uses, for example, for 1 gram of azelastine embonate:

0.005 to 600 g, preferably 300 g to 400 g of sweetener
0.01 to 10 g, preferably 0.2 to 0.4 g of flavoring Part of the amount of flavoring mentioned here can optionally also be added to the suspension later on.

BRIEF DESCRIPTION OF FIGURES OF DRAWING

In the drawings:

FIG. 1 is an infrared spectrum of azelastine ebonate and

FIG. 2 is a nuclear magnetic spectrum of azelastine ebonate.

DETAILED DESCRIPTION OF PREFERRED EMBODIMENTS

The following examples are illustrative of the invention.

EXAMPLE 1

Preparation of azelastine embonate

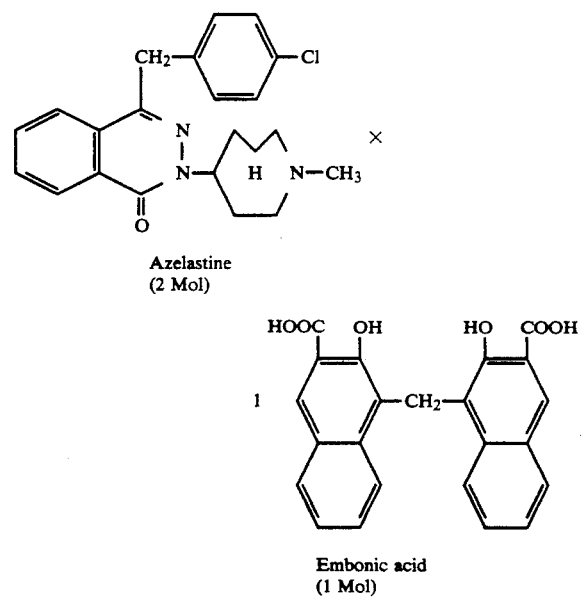

Azelastine
(2 Mol)

Embonic acid
(1 Mol)

177.5 g (1.01×2×0.21 mol) of azelastine hydrochloride are dissolved by stirring in 4,500 ml of ethanol 80% in a beaker. After addition of 90.6 g (0.21 mol) of embonic acid disodium salt the procedure is continued only until this has dissolved, ca. 4 minutes.

The resulting mixture is then immediately filtered through a fluted filter and the filtrate allowed to stand quietly overnight. The embonate precipitates out rapidly. The precipitate is suction filtered, washed with 80% ethanol and then with pure ethanol and dried in a vacuum for 20 hours at 60° C. Yield 195 g (80% of theory).

The product thereby obtained is stirred in ice water for 5 hours for further purification, suction filtered, washed first with ice water, then with ethanol and dried in a vacuum at 60° C. for 20 hours. Yield 195 g (80% of theory). The azelastine embonate is obtained in the form of a crystalline, weakly yellowish-colored powder. Melting point: 197° to 201° C.

The IR spectrum is shown in FIG. 1. For the nuclear magnetic resonance spectrum, see FIG. 2.

EXAMPLE 2

| Azelastine embonate suspension 3,000 ml of suspension (corresponding to 3,300 g) contain: | |
|---|---|
| Azelasting embonate | 3,600 g |
| Xanthane rubber | 21,000 g |
| Xylitol | 1,200,000 g |
| Sodium propyl-4-hydroxybenzoate (Na-salt of 4-hydroxybenzoic acid propyl ester) | 1,200 g |
| Sodium methyl-4-hydroxybenzoate (Na-salt of 4-hydroxybenzoic acid methyl ester) | 4,200 g |
| Hydrochloric acid 1 N | 21,000 g (a) |
| Raspberry flavoring | 0.900 g |
| Amaranth (Certified red dyestuff) | 0.150 g |
| Purified water | 2,047,950 g |
| | 3,300,000 g |

(a) The hydrochloric acid is required for adjustment of the pH value to 6.5. Use of hydrochloric acid deviating from the value given is compensated by corresponding reduction in the purified water used.

Preparation 800.0 g of xylitol and 21.0 xanthane rubber are dissolved in 2,000 g of water with stirring in a 3,000 ml beaker. The solution is then heated for 30 minutes at 115° C. in an autoclave. Following cooling to about 40° C., the solution is suction filtered under vacuum with recirculation into the working container of a homogenizing apparatus.

400.0 g of xylitol, 1.2 g of sodium propyl-4-hydroxybenzoate, 4.2 g of sodium methyl-4-hydroxybenzoate, 0.15 g of amaranth and 3.6 g of azelastine embonate are mixed in a porcelain dish and suction filtered into the previously prepared solution in the working container of the homogenizing apparatus.

0.9 g of raspberry flavoring and 21.0 g of hydrochloric acid are suction filtered under vacuum and with recirculation into the working container of the homogenizing apparatus. The suspension is homogenized for 15 minutes.

The pH value of the suspension so obtained is adjusted to 6.5 through addition of hydrochloric acid. The hydrochloric acid used is compensated by a reduced use of purified water. The formula for the calculation of the amount of water used is:

47.95 g—hydrochloric acid used in g = amount of water in g.

The suspension obtained is a viscous, red colored juice (pH value 6.3 to 6.7).

Active agent per 100 ml: 0.1200 g of azelastine embonate

Smell: of raspberries
Taste: raspberry flavor
Viscosity: 0.1–0.15 Pascal seconds (Pa.s.)

The juice (bulk liquid) is, for example, filled into screw-top brown glass bottles. The filling of the bulk liquid should be effected in such a manner that no air is entrapped through excessively fast pouring. The juice is, for example, stored at room temperature.

EXAMPLE 3

| Azelastine embonate suspension 5,000 ml of suspension corresponding to 5500 g contain: | |
|---|---|
| Azelastine embonate | 6,000 g (1) |
| Xanthane rubber | 32,500 g |
| Xylitol | 1,500,000 g |
| Sodium propyl-4-hydroxybenzoate | 2,000 g |
| Sodium methyl-4-hydroxybenzoate | 7,000 g |
| Embonic acid | 5,000 g |
| Raspberry flavoring | 1,500 g |
| Amaranth (red dyestuff) | 0.250 g |
| Citric acid | 64,000 g |
| Sodium hydroxide | 32,500 g |
| Purified water | 3,849,250 g (2) |
| | 5,500,000 g |

(1) The azelatine embonate was passed through a sieve of pore size 100 μm befor processing
(2) The pH value of the suspension is optionally adjusted with 1 N sodium hydroxide solution to 6.5. The consumption of sodium hydroxide solution is deducted from the water.

Method of preparation

I. 400 g of xylitol and 32.5 g of xanthane rubber are rubbed together and this mixture dissolved in 3,000 g of water with stirring. The solution is heated for 30 minutes at 115° C. in an autoclave. The water evaporating during autoclaving is replaced. After cooling to ca. 30° C. the solution is then transferred under vacuum and with recirculation into the working container of a homogenizing apparatus.

II. In the order listed, 64 g of citric acid, 5 g of embonic acid, 2 g of sodium propyl-4-hydroxybenzoate, 7 g of sodium methyl-4-hydroxybenzoate, 0.25 g of amaranth, 6 g of azelastine embonate, 1.5 g of raspberry flavoring and 1100 g of xylitol are suction filtered under vacuum with recirculation into the working container of a homogenizing apparatus. The pH value is optionally adjusted to 6.5 using 1N sodium hydroxide solution.

The result is flushed through with water and filled up to the final volume of 5,000 ml. The suspension is homogenized for 15 minutes under vacuum and recirculation.

The resultant suspension is a viscous red juice.
Viscosity = 0.1–0.15 Pascal seconds (Pa.s.)
pH value = 6.3–6.7
Density = 1.09–1.11 g/ml
Smell: of raspberries
Taste: raspberry flavor Azelastine embonate, processes for its preparation and pharmaceutical formulations which contain azelastine embonate as active substance.

What is claimed is:

1. Azelastine embonate.

2. A pharmaceutical composition comprising a therapeutically effective amount of azelastine embonate as active agent together with a pharmaceutically acceptable carrier.

3. A pharmaceutical composition comprising azelastine embonate as active agent together with a member of the group consisting of pharmaceutically acceptable auxiliary substances and diluents.

4. A dosage unit of the pharmaceutical composition of claim 2, said dosage unit containing 0.5–30 mg of azelastine embonate.

5. A pharmaceutical composition as set forth in claim 2 in which the carrier is an aqueous liquid in which azelastine ebonate is stably dispersed, said composition containing as active substance 3 to 3,000 mg azelastine embonate for each 100 ml of composition, said composition having a pH value of 3 to 9.

6. A pharmaceutical composition as set forth in claim 5 which contains a member of the group consisting of swelling agents, wetting agents, preservatives, sweeteners, flavorings and dyestuffs.

7. A pharmaceutical composition as set forth in claim 5 which contains, per 100 ml of composition, 0.001 to 30 g of preservatives (total amount), 0.005 to 60 g of sweetener, 0.001 to 1.0 g of dyestuff as well as 0.001 to 10 g of flavoring.

8. A pharmaceutical composition as set forth in claim 5 in which up to 60 percent by weight of the aqueous liquid comprises a physiologically acceptable liquids which is miscible with water.

9. A pharmaceutical composition as set forth in claim 5 which contains 1 to $10^{-5}$ g of wetting agent (for each 100 ml of final suspension).

10. An aerosol container having a metering valve which is constructed and arranged to release 0.025 to 0.1 ml of liquid per actuation, said container containing the suspension of claim 5 and a propellant.

11. A solid formulation comprising the pharmaceutical composition of claim 2 which contains 0.5 to 30 mg of azelastine embonate and the carrier being at least one auxiliary substance selected from the group consisting of starch, cellulose, cellulose ether, sugar, hexitol, calcium hydrogen phosphate, calcium phosphate, modified starch, alginate, pectin, carboxymethylcellulose, ultraamylopectin, bentonite, polyvinylpyrrolidone, gelatin and vinylpyrrolidone vinyl acetate copolymerizate.

12. A method of treating the symptoms of asthma or protecting against asthmatic symptoms in a person susceptible to asthma which comprises administering a therapeutically effective amount of azelastine embonate.

* * * * *